United States Patent [19]

Kawa et al.

[11] Patent Number: 5,494,938
[45] Date of Patent: Feb. 27, 1996

[54] OIL-IN-WATER EMULSIONS

[75] Inventors: Rolf Kawa, Monheim; Achim Ansmann, Erkrath; Manfred Weuthen, Solingen; Holger Tesmann, Duesseldorf; Thomas Foerster, Erkrath, all of Germany

[73] Assignee: Henkel Kommanditgesellschaft auf Aktien, Duesseldorf, Germany

[21] Appl. No.: 39,467

[22] PCT Filed: Oct. 16, 1991

[86] PCT No.: PCT/EP91/01966

§ 371 Date: Apr. 26, 1993

§ 102(e) Date: Apr. 26, 1993

[87] PCT Pub. No.: WO92/07543

PCT Pub. Date: May 14, 1992

[30] Foreign Application Priority Data

Oct. 25, 1990 [DE] Germany ............ 40 33 928.9

[51] Int. Cl.⁶ .................. A61K 9/12; A61K 47/00
[52] U.S. Cl. .................. 514/786; 514/844; 514/847; 514/938
[58] Field of Search .................. 514/938, 786

[56] References Cited

U.S. PATENT DOCUMENTS 4,400,295  8/1983  Ootsu et al. .................. 252/312
4,847,078  7/1989  Sheppard et al. .................. 514/777

FOREIGN PATENT DOCUMENTS 0428157     5/1991  European Pat. Off. .................. 514/938
61-005005   1/1986  Japan .................. 514/938
1115014     6/1986  Japan .................. 424/63
1203036     8/1989  Japan .................. 514/938

OTHER PUBLICATIONS

Chemical Abstracts, vol. 84, No. 7, Columbus; Ohio, US; Niiya, I et al.: "Effects of Emulsifiers on the Crystal Growth of Edible Solid Fats. IV. Effects of Propylene Glycol Esters of Fatty Acids and Unsaturated Fatty Acid Monoglycerides." (Abstract).
Triton CG–110 Technical Bulletin, Rohm & Haas, Philadelphia, Pa., May 1975.
A. J. O'Lenick, Jr., et al., "Guerbet Alcohols, A Versatile Hydrophobe", *Soap Cosm. Chem. Spec.*, Apr., 1987, pp. 52, 54, 55, 115.

*Primary Examiner*—Dale R. Ore
*Attorney, Agent, or Firm*—Wayne C. Jaeschke; John E. Drach; Henry E. Millson, Jr.

[57] ABSTRACT

This invention relates to storage oil-in-water emulsions, hereinafter referred to as 0/w emulsions, containing alkyl glucosides and a partial glyceride with a monoglyceride content of 60–95% by weight and to emulsifier concentrates containing alkyl glucosides, a partial glyceride with a monoglyceride content of 60 to 95% by weight and a long-chain alcohol.

12 Claims, No Drawings

5,494,938

OIL-IN-WATER EMULSIONS

BACKGROUND OF THE INVENTION

1. Field of the Invention

This invention relates to storable oil-in-water emulsions, hereinafter referred to as o/w emulsions, containing alkyl glucosides and a partial glyceride with a monoglyceride content of 60 to 95% by weight and to emulsifier concentrates containing alkyl glucosides, a partial glyceride with a monoglyceride content of 60 to 95% by weight and a long-chain alcohol.

2. Statement of Related Art

The use of alkyl glucosides in the field of cosmetics is known from the literature. Thus, in their TRITON CG-110 pamphlet, Rohm & Haas recommend the use of an alkyl glucoside based on octanol/decanol (50:50) as an auxiliary emulsifier for cosmetic emulsions, for example for skin creams and lotions. Japanese patent application JP 89/203 036 (Shiseido) describes cosmetic emulsions containing a $C_{8-24}$ glucoside together with a polyol containing at least three hydroxyl groups, for example glycerol, and an oil component. Finally, JP 86/5005 (Yoshitomi Pharm.) Ind. describes the use of alkyl ($C_{8-18}$) glucosides as moisturizers, for example in cosmetic creams.

Alkyl glucosides are suitable as emulsifiers for the production of o/w emulsions. It has been found that the alkyl glucosides present in such emulsions have a pronounced tendency to crystallize which cannot be suppressed even by nonionic, anionic or cationic co-emulsifiers. Macroscopically, crystal growth is reflected in a deterioration in structure. Crystal structures such as these destroy the homogeneous droplet distribution which results in unwanted destabilization and, finally, in breaking of the emulsions. Accordingly, the problem addressed by the present invention was to provide storable o/w emulsions containing alkyl glucosides.

DESCRIPTION OF THE INVENTION

According to the invention, this problem has been solved by oil-in-water emulsions containing alkyl glucosides, characterized in that they contain (A) one or more water-insoluble oils, (B) as emulsifier, one or more alkyl glucosides corresponding to the general formula $RO(G)_x$, in which
R is a linear saturated $C_{8-22}$ alkyl radical
G is a glucose unit
is a number of 1 to 10, characterized in that they contain (C) a fatty acid partial glyceride with a monoglyceride content of 60 to 95% by weight as crystallization inhibitor.

In one preferred embodiment of the invention, the emulsions according to the invention contain the water-insoluble oil (A) in a quantity of 5 to 30% by weight, the alkyl glucoside (B) in a quantity of 2 to 15% by weight and the fatty acid partial glyceride (C) in a quantity of 2 to 20% by weight.

The o/w emulsions according to the invention show no crystals of alkyl glucosides under a light microscope, even with 400x magnification. The emulsions are homogeneous and stable in storage.

Basically, any water-insoluble, linear or branched, physiologically safe aliphatic hydrocarbons, ethers or esters liquid at room temperature (20° C.) may be used as the oil(s) (A). However, solid or relatively high melting paraffins, esters, waxes or fats may also be used.

Particularly suitable oils from the group of aliphatic hydrocarbons are, for example, squalane, squalene, dioctyl cyclohexane, Paraffinum perliquidum and Paraffinum subliquidum and isohexadecane (hydrogenated polybutylene).

Other particularly suitable oils are esters of trihydric and more than trihydric alcohols, more particularly vegetable triglycerides, for example olive oil, almond oil, peanut oil, sunflower oil, or even the esters of pentaerythritol, for example with pelargonic acid or oleic acid.

Other particularly suitable oils are monoesters and diesters corresponding to general formulae I, II and III

$$R^1\text{—COOR}^2 \quad (I)$$

$$R^2\text{—OOC—}R^3\text{—COOR}^2 \quad (II)$$

$$R^1\text{—COO—}R^3\text{—OOC—}R^1 \quad (III)$$

in which $R^1$ is a $C_{8-22}$ alkyl group, $R^2$ is a $C_{3-22}$ alkyl group and $R^3$ represents $C_{2-16}$ alkylene groups. These monoesters and diesters contain at least 11 and at most 40 carbon atoms.

Oils of the mono and diester type corresponding to formulae (I), (II) and (III) are known as cosmetic and pharmaceutical oil components and as lubricant components. Among the monoesters and diesters of this type, the products liquid at room temperature (20° C.) are the most important. Monoesters (I) suitable as oils are, for example, the isopropyl esters of $C_{12-22}$ fatty acids such as, for example, isopropyl myristate, isopropyl palmitate, isopropyl stearate, isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyl dodecyl palmitate, oleyl oleate, oleyl erucate, erucyl oleate and esters obtainable from technical aliphatic alcohol mixtures and technical aliphatic carboxylic acids, for example esters of saturated and unsaturated $C_{12-22}$ fatty alcohols and saturated and unsaturated $C_{12-22}$ fatty acids which are obtainable from animal and vegetable fats. Naturally occurring monoester or wax ester mixtures, as present for example in jojoba oil or sperm oil, are also suitable.

Suitable dicarboxylic acid esters (II) are, for example, di-n-butyl adipate, di-n-butyl sebacate, di-(2-ethylhexyl)-adipate, di-(2-hexyldecyl)-succinate and diisotridecyl azelate. Suitable diol esters (III) are, for example, ethylene glycol dioleate, ethylene glycol diisotridecanoate, propylene glycol di-(2-ethylhexanoate), propylene glycol diisostearate, propylene glycol dipelargonate, butanediol diisostearate and neopentyl glycol dicaprylate.

Other suitable oils are branched primary alcohols of the type known as Guerbet alcohols (see, for example, A. J. O'Lenick Jr., R. E. Bilbo, Soap Cosm. Chem. Spec. 1987, 52), for example 2-hexyl decanol or 2-octyl dodecanol, and esters of Guerbet alcohols with long-chain aliphatic carboxylic acids, for example with stearic acid.

The oils are used in the o/w emulsions according to the invention in a quantity of 5 to 30% by weight and, more particularly, 10 to 20% by weight.

Suitable alkyl glucosides (B) are glucosides containing a $C_{8-22}$ alkyl radical. They are normally prepared by reaction of glucose or starch or starch syrup with the corresponding long-chain alcohols. The alcohols have to be used in excess.

On completion of the reaction, the unreacted alcohol is largely distilled off, so that the alkyl glucoside used in accordance with the invention generally has residual alcohol contents of approximately 1% by weight.

Alkyl glucosides are characterized by the general formula $RO(G)_x$, in which:

is a linear saturated $C_{8-22}$ alkyl radical

G is a glucose unit x is a number of 1 to 10.

The index x is the degree of oligomerization and represents a mean value for the distribution of monoglucosides and oligoglucosides. As a calculated quantity, the degree of oligomerization says something of the distribution of the chemical individuals present in a technical oligomer mixture which differ from one another in the number of glucose units present per molecule alkyl glucoside. The average degree of oligomerization x should be a value of 1.1 to 1.6.

In another preferred embodiment of the invention, the alkyl radical of the alkyl glucoside has a chain length of 12 to 18 carbon atoms and more particularly 16 to 18 carbon atoms. Alkyl glucosides containing at least 85% by weight $C_{16}$ are particularly suitable. The alkyl glucosides used in accordance with the invention are species of which the alkyl radicals have the preferred chain lengths mentioned. However, they may also contain small quantities of species where the alkyl radicals have shorter and/or longer chain lengths, as present for example in the alkyl radicals of fatty alcohols of vegetable and animal origin.

In a particularly preferred embodiment, alkyl glucosides having a degree of oligomerization x of 1.1 to 1.3 are used.

Another preferred embodiment of the present invention is characterized in that, in addition to the components described above, it also contains a consistency regulator. Consistency regulators are substances which determine or maintain the consistency of cosmetic preparations, for example emulsions (cf. H. Fey, I. Otte, "Wörterbuch der Kosmetik", Stuttgart 1985). Long-chain alcohols, carboxymethyl cellulose or salts of polyacrylic acids, for example, may be used as consistency regulators in the o/w emulsions according to the invention. Alcohols containing 14 to 22 carbon atoms and, more particularly, 16 to 18 carbon atoms are particularly suitable as consistency regulators. The consistency regulators may advantageously be introduced in the form of the alcohol which is present in the alkyl glucoside after partial removal of the unreacted alcohol by distillation.

The temperatures to which the alkyl glucosides are exposed during removal of the unreacted alcohol by distillation can readily result in unwanted brownish discoloration which necessitates a bleaching process. Accordingly, it can be of advantage not to remove too much of the reacted alcohol, particularly when the long-chain alcohol is in any case to be used as consistency regulator in the o/w emulsion. Accordingly, another embodiment of the present invention is characterized by the use of a crude alkyl glucoside containing 1 to 20% by weight and preferably 2.5 to 5% by weight unreacted alcohol.

The alkyl glucosides are used in the o/w emulsions according to the invention in a quantity of 2 to 15% by weight and, more particularly, in a quantity of 2 to 7% by weight.

Fatty acid partial glycerides (C) of saturated or unsaturated $C_{10-20}$ fatty acids are technical mixtures of fatty acid mono-, di- and triglycerides which are obtained by esterification of 1 mol glycerol with 1 to 2 mol of a ($C_{10-20}$) fatty acid or by transesterification of 1 mol of a ($C_{10-20}$) fatty acid triglyceride, for example beef tallow, lard, palm oil, sunflower oil or soybean oil, with 0.5 to 2 mol glycerol.

Two types of partial glycerides are commercially obtainable. Partial glycerides of type I contain 35 to 60% monoglycerides, 35 to 50% diglycerides and 1 to 20% triglycerides. Partial glycerides of type II are prepared by molecular distillation from those of type I and contain 90 to 95% monoglycerides, 1 to 5% diglycerides and less than 1% triglycerides (cf.: a) G. Schuster and W. Adams: Zeitschrift für Lebensmitteltechnologie, 1979, Vol. 30 (6), pages 256–264; b) G. Schuster (Ed.) "Emulgatoren für Lebensmittel", Springer-Veralg, 1985).

The fatty acid partial glycerides used in accordance with the invention should contain 60 to 95% monoglycerides, 1 to 35% diglycerides and 0.1 to 5% triglycerides. A preferred embodiment of the invention is characterized by the use of fatty acid partial glycerides containing 90 to 95% by weight monoglyceride. Fatty acid partial glycerides of which the fatty acid components contain 16 to 18 carbon atoms are particularly favorable.

The fatty acid partial glycerides are used in the o/w emulsions according to the invention in a quantity of 2 to 20% by weight and, more particularly, in a quantity of 4 to 10% by weight.

In addition, the o/w emulsions according to the invention may contain additional components or auxiliaries known from the prior art. The most important are:

a) co-emulsifiers, for example anionic surfactants containing carboxylate, sulfonate, sulfate or phosphate groups, such as soaps, alkyl and aryl ether sulfates, fatty amines, quaternary ammonium and pyridinium compounds, nonionic emulsifiers, such as ethylene oxide adducts with alcohols, carboxylic acids, partial glycerides and sorbitan esters, amphoteric emulsifiers, such as imidazo line derivatives., betaines or sulfobetaines and, for example, fatty acid esters and sorbitan fatty acid esters (cf., for example, W. Umbach [Ed.], "Kosmetik-Entwicklung, Herstellung und Anwendung kosmetischer Mittel", pages 86–87, Stuttgart 1988).

b) Humectants, for example glycerol, polyglycerols, sorbitol, propane-1,2-diol, butane-1,2,3-triol, polyethylene glycols, glucose, mannitol, xylitol.

c) Antimicrobial agents as preservatives, for example benzoic acid, salicylic acid, sorbic acid and esters and salts thereof.

d) Perfume oils, for example natural fragrances obtained by distillation, extraction or pressing from plants and synthetic fragrances (cf., for example, H. Aebi, E. Baumgartner, H. P. Fiedler, G. Ohloff, "Kosmetika, Riechstoffe und Lebensmittelzusatzstoffe", Stuttgart 1978).

e) Antioxidants, for example tocopherols, lecithin, guaiacol, butyl cresol, 4-methyl-2,6-ditert.butyl phenol (BHT), 4-methoxy-2(3)-tert.butyl phenol (BHA)

f) Dyes of the type listed for cosmetics, for example, by the Farbstoff Kommission der Deutschen Forschungsgemeinschaft ("Färbemittel für Kosmetika", Mitteilung 3, Wiesbaden 1968).

To prepare the emulsions, the alkyl glucosides are dissolved either in the hot water phase or fatty phase. The water phase is preferably added to the oil phase with stirring at 60° to 80° C. The dispersions thus obtained are subsequently cooled to 30° C. If desired, the structure of the emulsion may be improved during cooling by units operating on the rotor/stator principle, for example Ultra-Turrax T50 (Ika-Werke).

The o/w emulsions according to the invention may also be prepared in the absence of heat by virtue of the solubility of the alkyl glucosides in water, particularly those containing $C_{12-16}$ alkyl radicals. Rich liquid or creamy cosmetic emulsions can be formulated in this way, particularly in combination with hydrophilic or hydrophobic emulsifiers and oils liquid at room temperature, using polymeric thickeners.

The present invention relates to emulsifier concentrates for the production of o/w emulsions according to the invention containing (D) 24 to 75% by weight of one or more alkyl glucosides corresponding to the general formula $RO(G)_x$, in which
   R is a linear saturated $C_{8-22}$ alkyl radical
   G is a glucose unit
   x is a number of 1 to 10

(E) 24 to 75% by weight of a fatty acid partial glyceride containing 60 to 95% by weight monoglyceride (F) 0.1 to 50% by weight of a linear saturated alcohol containing 14 to 22 carbon atoms and, more particularly, 16 to 18 carbon atoms.

For the reasons mentioned above, the emulsifier concentrates may also be prepared using alkyl glucosides in whose case unreacted alcohol was distilled off only partly, if at all, during the production process. Accordingly, a preferred embodiment of the present invention is characterized in that the emulsifier concentrates are prepared using alkyl glucosides containing from 3 to 90% by weight and preferably from 3 to 40% by weight unreacted alcohol. In cases such as these, the alkyl glucosides may be mixed with the fatty acid partial glycerides immediately after the reaction between glucose and long-chain alcohols and, if desired, partial removal of the unreacted alcohol by distillation at temperatures of around 100° C. It is possible in this way to produce self-emulsifying emulsion bases with which cosmetically sophisticated creams and lotions can be formulated.

In addition, the emulsifier concentrates according to the invention may contain additional components or auxiliaries of the type described above, for example oils, co-emulsifiers, humectants, preservatives, perfume oils, antioxidants, dyes.

The following Examples are intended to illustrate the invention.

EXAMPLES

1. Substances used 1.1 oil (A)

Cetiol V: oleic acid decyl ester (Henkel KGaA, Düsseldorf); Myritol 318: caprylic/capric acid triglyceride (Henkel KGaA, Düsseldorf)

1.2 Alkyl glucosides (B)

The alkyl glucosides used were $C_{14}$, $C_{16}$ and $C_{18}$ alkyl glucosides (abbreviated to AG C14, AG C16 and AG C18) having degrees of oligomerization x of 1.2 to 1.4. The corresponding $C_{14}$, $C_{16}$ and $C_{18}$ fatty alcohols were used to prepare the $C_{14}$, $C_{16}$ and $C_{18}$ alkyl glucosides (C chain distribution according to GC: a) for $C_{14}$ fatty alcohol: 2% $C_{12}$; 96% $C_{14}$; 2% $C_{16}$; b) for $C_{16}$ fatty alcohol: 2% $C_{14}$; 96% $C_{16}$; 2% $C_{18}$; c) for $C_{18}$ fatty alcohol: 2% $C_{16}$; 96% $C_{18}$; 2% $C_{20}$).

1.3 Fatty acid partial glycerides (C)

Cutina MD: fatty acid partial glyceride based on hydrogenated palm oil with a monoglyceride content of 42% by weight (Grünau, Illertissen); Monomuls 60–35: fatty acid partial glyceride based on hydrogenated palm oil with a monoglyceride content of 60% by weight (Grünau, Illertissen); Monomuls 90–35: fatty acid partial glyceride based on hydrogenated palm oil with a monoglyceride content of 90% by weight (Grünau, Illertissen)

1.4 Other components Lanette O: cetyl/stearyl alcohol [50:50](Henkel KGaA, Düsseldorf); Lanette E: cetyl/stearyl alcohol sulfate, Na salt [50:50](Henkel KGaA, Düsseldorf); Cutina E-24: polyoxyethylene-24-glycerol monostearate (Henkel KGaA, Düsseldorf).

2. Production and characterization of the dispersions

To prepare the emulsions, the alkyl glucosides were dissolved in either the hot water phase or fatty phase. The water phase was preferably added with stirring to the oil phase at 60° to 80° C. The dispersions obtained were then cooled to 30° C.

After 24 hours, the viscosities were measured at 23° C. with a Brookfield viscositmeter using spindle E at 4 r.p.m. The emulsions were then stored for 2 weeks at −5° C., 20° C. and 40° C. and examined visually and under a microscope (400× magnification). The results are shown in Table 1 according to the composition of the emulsions.

In every case where Monomuls 90–35 or Monomuls 6–35 (monoglyceride content: 90% or 60%) was used as the partial glyceride, the emulsions obtained were homogeneous both immediately after preparation and after storage under the conditions described above (Table 1, columns B1 to B8). By contrast, the emulsion obtained using Cutina MD, a partial glyceride containing 42% monoglyceride, was either homogeneous immediately after its preparation, but showed distinctly crystalline constituents under a light microscope (400× magnification) and separated into two phases at 40° C. (Table 1, columns C1 and C2), or was macroscopically inhomogeneous immediately after its preparation (Table 1, column C3).

TABLE 1

| | o/w emulsions | | | | | | | | | | |
|---|---|---|---|---|---|---|---|---|---|---|---|
| | C1 | C2 | V3 | B1 | B2 | B3 | B4 | B5 | B6 | B7 | B8 |
| AG C14 (x = 1.4) | — | 4.0 | — | — | — | — | — | — | 4.0 | — | — |
| AG C16 (x = 1.2) | 4.0 | — | — | 4.0 | — | — | — | — | — | — | — |
| AG C16 (x = 1.3) | — | — | — | — | 4.0[1)] | 4.0 | 4.0 | 4.0 | — | — | 4.0[5)] |
| AG C18 (X = 1.4) | — | — | 4.0 | — | — | — | — | — | — | 4.0 | — |
| Monomuls 90-35 | — | — | — | 5.6 | 5.0[1)] | — | 7.0 | 7.0 | 5.6 | 7.0 | 4.0[5)] |
| Monomuls 60-35 | — | — | — | — | — | 5.6 | — | — | — | — | — |
| Cutina ND | 5.6 | 5.6 | 7.0 | — | — | — | — | — | — | — | — |
| Cetiol V | 14.0 | 14.0 | 12.0 | 14.0 | 14.0 | 14.0 | 12.0 | — | 14.0 | 12.0 | 14.0 |
| Myritol 318 | — | — | — | — | — | — | — | 12.0 | — | — | — |
| Stearyl alcohol | — | — | — | — | — | — | — | — | — | — | 0.8[5)] |
| Cetyl alcohol | — | — | — | — | 1.0[1)] | — | — | — | — | — | 1.0 |
| Lanette 0 | 0.8 | 0.8 | — | 0.8 | — | 0.8 | — | — | 0.8 | — | — |
| Glycerol 86% | 3.0 | 3.0 | 3.0 | 3.0 | 3.0 | 5.0 | 5.0 | 5.0 | 3.0 | 3.0 | 3.0 |

TABLE 1-continued

| | o/w emulsions | | | | | | | | | | |
|---|---|---|---|---|---|---|---|---|---|---|---|
| | C1 | C2 | V3 | B1 | B2 | B3 | B4 | B5 | B6 | B7 | B8 |
| Lanette E | — | — | — | — | — | — | — | 0.5 | — | — | — |
| Cutina E-24 | — | — | — | — | — | — | — | — | 1.0 | — | — |
| Water, preservative | ad 100 | ad 100 | ad 100 | ad 100 | ad 100 | ad 100 | ad 100 | ad 100 | ad 100 | ad 100 | ad 100 |
| Viscosity [Pas] | 180 | 190 | 75 | 100 | 140 | 150 | 250 | 250 | 150 | 100 | 100 |
| Appearance after storage at: | | | | | | | | | | | |
| −5° C. | hom[2] | hom | inhom[4] | hom | hom | hom | hom | hom | hom | hom | hom |
| 20° C. | hom | hom | inhom | hom | hom | hom | hom | hom | hom | hom | hom |
| 40° C. | sep.[3] | sep. | sep. | hom | hom | hom | hom | hom | hom | hom | hom |

[1] Example B2 was prepared from an emulsifier concentrate consisting of a 1:1 mixture of AG C16 (residual alcohol content: 20%) and Monomuls 60-35
[2] hom = homogeneous
[3] sep. = separation
[4] inhom = inhomogeneous
[5] Example B8 was prepared from an emulsifier concentrate consisting of a mixture of 40% AG C16 (residual alcohol content 20%), 52% Monomuls 90-35 and 8% stearyl alcohol.

What is claimed is:

1. An oil-in-water emulsion comprising: (A) from about 5% to about 30% by weight of a water insoluble oil which is a linear or branched, physiologically safe, aliphatic hydrocarbon, ether, or ester, liquid at room temperature, or a solid or higher melting paraffin, ester, wax or fat; (B) from about 2 to about 15% by weight of an alkyl glucoside of the formula $$RO(G)_x$$

wherein R is a linear saturated $C_{8-22}$ alkyl radical, G is a glucose unit, and x is a number from 1 to about 10; and (C) from about 2 to about 20% by weight of a mixture of a fatty acid partial glyceride of saturated or unsaturated $C_{10-20}$ fatty acids having a monoglyceride content of from about 60% to about 95% by weight.

2. The composition of claim 1 wherein said water-insoluble oil (A) is present in a quantity of from about 10% to about 20% by weight, said alkyl glucoside (B) is present in a quantity of from about 2% to about 7% by weight and said fatty acid partial glyceride (C) is present in a quantity of from about 4% to about 10% by weight.

3. The composition of claim 1 wherein in component (B) R is a linear saturated $C_{16-18}$ alkyl radical.

4. The composition of claim 1 wherein in component (B) x is from about 1.1 to about 1.6.

5. The composition of claim 1 further comprising a $C_{14-22}$ alcohol.

6. The composition of claim 5 wherein said alcohol is a $C_{16-18}$.

7. The composition of claim 1 wherein component (A) is an aliphatic hydrocarbon; an ester of a trihydric or higher alcohol; a monoester or diester of the formulae:

$$R^1\text{—COOR}^2 \quad (I)$$

$$R^2\text{—OOC—}R^3\text{—COOR}^2 \quad (II)$$

$$R^1\text{—COO—}R^3\text{—}R^1 \quad (III)$$

in which $R^1$ is a $C_{8-22}$ alkyl group, $R^2$ is a $C_{3-22}$ alkyl group and $R^3$ represents a $C_{2-16}$ alkylene group, and the monoester or diester contains from 11 to 40 carbon atoms; or a Guerbet alcohol or a long chain aliphatic carboxylic acid ester thereof.

8. The composition of claim 1 wherein in component (B) x is from about 1.1 to about 1.3.

9. The composition of claim 1 wherein in component (C) the monoglyceride content is from about 90 to about 95% by weight.

10. The composition of claim 1 wherein component (A) is an aliphatic hydrocarbon; an ester of a trihydric or higher alcohol; a monoester or diester of the formulae:

$$R^1\text{—COOR}^2 \quad (I)$$

$$R^2\text{—OOC—}R^3\text{—}COOR2 \quad (II)$$

$$R^1\text{—COO—}R^3\text{—OOC—}R^1 \quad (III)$$

in which $R^1$ is a $C_{8-22}$ alkyl group, $R^2$ is a $C_{3-22}$ alkyl group and $R^3$ represents a $C_{2-16}$ alkylene group, and the monoester or diester contains from 11 to 40 carbon atoms; or a Guerbet alcohol or a long chain aliphatic carboxylic acid ester thereof; and in component (B) R is a linear saturated $C_{12-18}$ alkyl radical and x is from about 1.1 to about 1:6.

11. The composition of claim 10 wherein in component (B) x is from about 1.1 to about 1.3; and in component (C) the monoglyceride content is from about 90 to about 95% by weight.

12. The composition of claim 10 further comprising a $C_{14-22}$ alcohol.

* * * * *